United States Patent
McDonald

(10) Patent No.: US 6,837,238 B2
(45) Date of Patent: *Jan. 4, 2005

(54) LIGHTWEIGHT OXYGEN DELIVERY DEVICE FOR PATIENTS

(75) Inventor: Lee McDonald, Barrie (CA)

(73) Assignee: Southmedic Incorporated (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/186,015

(22) Filed: Jul. 1, 2002

(65) Prior Publication Data

US 2004/0094160 A1 May 20, 2004

Related U.S. Application Data

(63) Continuation-in-part of application No. 09/977,148, filed on Oct. 12, 2001, now Pat. No. 6,675,796.

(51) Int. Cl.$^7$ .......................... A62B 29/00; A62B 37/00; F24F 13/00
(52) U.S. Cl. .............................. 128/200.28; 128/207.11
(58) Field of Search ....................... 128/200.24, 200.26, 128/200.28, 201.19, 203.29, 204.11, 204.12, 205.11, 207.14, 207.17, 207.18, 207.11, 205.25, 206.21, 206.27, DIG. 26

(56) References Cited

U.S. PATENT DOCUMENTS

| | | | | |
|---|---|---|---|---|
| 3,677,250 A | * | 7/1972 | Thomas | 604/180 |
| 3,977,407 A | * | 8/1976 | Coleman et al. | 604/179 |
| 4,142,527 A | * | 3/1979 | Garcia | 604/180 |
| 4,465,067 A | * | 8/1984 | Koch et al. | 128/207.18 |
| 4,593,688 A | | 6/1986 | Payton | |
| 4,932,943 A | * | 6/1990 | Nowak | 604/180 |
| 4,986,815 A | * | 1/1991 | Schneider | 604/180 |
| 5,156,641 A | * | 10/1992 | White | 128/207.18 |
| 5,443,060 A | * | 8/1995 | Visveshwara et al. | 128/200.26 |
| 5,718,225 A | * | 2/1998 | Visveshwara et al. | 128/200.26 |
| 5,735,272 A | * | 4/1998 | Dillon et al. | 128/207.18 |
| 5,752,511 A | * | 5/1998 | Simmons et al. | 128/207.18 |
| 5,833,663 A | * | 11/1998 | Bierman et al. | 604/174 |
| 5,931,854 A | * | 8/1999 | Dillon | 606/204.45 |
| 6,065,473 A | * | 5/2000 | McCombs et al. | 128/204.18 |
| 6,247,470 B1 | * | 6/2001 | Ketchedjian | 128/200.28 |
| D449,376 S | * | 10/2001 | McDonald et al. | D24/110 |
| D449,883 S | * | 10/2001 | McDonald et al. | D24/110 |
| 6,450,166 B1 | | 9/2002 | McDonald et al. | |
| 6,595,207 B1 | * | 7/2003 | McDonald et al. | 128/200.28 |

* cited by examiner

*Primary Examiner*—Henry Bennett
*Assistant Examiner*—Kathryn Odland
(74) *Attorney, Agent, or Firm*—Nikolai & Mersereau, P.A.

(57) ABSTRACT

A lightweight oxygen delivery device is provided for a patient is provided, the device comprising an elongated tube bendable to a particular shape and capable of maintaining that shape. The tube is adapted to carry oxygen and has a first end and a second end. The first end is releasably connectable to an oxygen delivery source. To the second end of the tube is secured an end of a rigid elbow. One of those ends being secured to the second end of the tube and an oxygen diffuser connected to the other end of the elbow. An oxygen diffuser is connected to that other end of the elbow. The diffuser comprises a body having a wall, the interior surface of which wall is of generally concave configuration. The wall circumscribes a centrally positioned oxygen outlet communicating with that other end of the elbow so as to receive oxygen from the elbow and direct the flow of oxygen delivered from the elbow generally towards the patient's nose and mouth. Flexible wings are secured to the tube, between its ends, the wings extending outwardly to either side. An elongated flexible strap is secured to and extends between the wings, the strap to extend around a patient's head and secure the wings in position to hold the diffuser proximal to the patient's nose and mouth.

9 Claims, 3 Drawing Sheets

LIGHTWEIGHT OXYGEN DELIVERY DEVICE FOR PATIENTS

RELATED APPLICATION

The present invention is a continuation in part of applicant's application Ser. No. 09/977,148 filed Oct. 12, 2001 now U.S. Pat. No. 6,675,796.

FIELD OF THE INVENTION

The present invention relates to a novel system for delivery of oxygen to a patient and more particularly to a system which can be used to replace conventional oxygen masks and nose cannula oxygen delivery systems.

BACKGROUND OF THE INVENTION

The present invention is related to, but different from, those described co-pending U.S. patent applications Ser. No. 09/572,637 entitled, PATIENT OXYGEN DELIVERY SYSTEM filed May 17, 2000 and Ser. No. 09/659,503 entitled, OXYGEN DIFFUSER FOR PATIENT OXYGEN DELIVERY SYSTEM filed Sep. 11, 2000.

Common problems with a conventional oxygen mask include:
1. Some patients find it claustrophobic.
2. Many patients cannot tolerate the smell of plastic resin.
3. Patients must take the mast off to speak or eat thereby discontinuing therapy.
4. Some patients are allergic to the elastic (latex allergy).
5. Some patients feel ill when they wear an oxygen mask, (the psychological effect is truly remarkable on the patient and the patient's family alike).
6. Patients often aspirate if they vomit while wearing the mask.
7. The mask cannot be used during facial surgery due to intrusions into the sterile field.
8. The mask cannot be worn if the patient has facial injuries such as burns.
9. Skin irritation is often found from the plastic.
10. The face mask does not effectively fit all sizes and shapes of face. Often the soft plastic masks are delivered in a deformed fashion.
11. The face mask usual necessitates clipping the oxygen delivery tube in front of the patient at the bottom of the mask. This is awkward and inconvenient as it may interfere with a patient's movement.
12. The face mask creates irregular infusion of oxygen by the patient, with exhaled air from the patient being mixed with oxygen in the mask.

Another current approach to oxygen delivery to a patient employs an oxygen delivery tube with tubular, open ended nasal prongs or cannula at the delivery end of the tube for insertion into a patient's nasal passages. Disadvantages of nasal cannulas include:
1. The patient may not be a nose breather.
2. Patents often get nose bleeds from the dryness of the nasal cannulas.
3. Patients find the front oxygen cord, necessary with nasal cannulas, difficult to handle as it hangs down directly in front of them and applies downward pressure on their ears, where it is suspended.

Of background interest is U.S. Pat. No. 4,593,688 of Payton issued Jun. 10, 1986, which describes and illustrates a tubular system for, example, delivery nebulized oxygen enriched fog or the like to the face and mouth of a croup patient, the tube being suspended, at its delivery end, from a series of straps secured about a patient's head. A portion of the tube is mounted on a pivoting, u-shaped frame member so that the tubing is held in front of and below the patient's face, for delivery of the nebulized oxygen enriched fog. The gas delivery to the nose and mouth area of the patient is through orifices in the tube, near the patient's nose and mouth when the tube is in position. This system is intended for children, and would be uncomfortable and restrictive to one's movements, if placed in position on a patient for a long period of time.

In applicant's co-pending application Ser. No. 09/572,637, there is described a lightweight oxygen delivery system comprising a headband or an ear support to be comfortably seatably engaged over a patient's head or ear. A clip is secured to the headband or ear support. One end of an elongated tubular boom is secured to the clip to extend and hold its position, when in operation, so that its other end is located at a space in front of, and proximal, to the patient's nose and mouth. An oxygen diffuser is secured to that other end, to deliver oxygen from the boom to the space in the vicinity of the patient's nose and mouth. The clip is constructed so as to hold securely an oxygen delivery tube from an oxygen source in fluid communication with the one end of the boom so as to deliver oxygen from the source to the boom for discharge through the diffuser.

In applicant's co-pending application Ser. No. 09/659,503, an oxygen diffuser for such a system is described and illustrated, the diffuser comprising a body having a wall, the interior surface of which wall is generally of concave configuration and circumscribes a centrally positioned oxygen outlet so as to direct the flow of oxygen from the outlet generally towards the patient's nose and mouth. A baffle is seated over the oxygen outlet so as to assist in mixing of oxygen with ambient air and avoid a direct flow of oxygen towards the patient's face.

In applicant's copending application Ser. No. 09/977,148, a lightweight oxygen delivery system is described and illustrated comprising an oxygen diffuser mounted on an elbow at the end of an oxygen delivery tube. A flexible attachment surface is secured to the tube, between its ends, the attachment surface carrying a skin adhesive for releasable attachment to the patient's chin or cheek, so as to position the diffuser proximal to the patient's nose and mouth.

The present invention provides an alternative construction for securing such a lightweight oxygen delivery system on a patient's head.

SUMMARY OF THE INVENTION

There is a need for a lightweight oxygen delivery system, which can replace a face mask or a nasal cannula system, which is economical to manufacture and effective in operation. There is also a need for such a system to be versatile in the manner in which it secures to a patient's head. As well, from time to time, the carbon dioxide level in a patient's exhaled breath must be monitored. It is thus an object of one embodiment of the present invention to provide a lightweight, economical combination oxygen delivery and carbon dioxide monitoring system.

In accordance with the present invention there is provided a lightweight oxygen delivery device for a patient comprising an elongated tube which is bendable to a particular shape and capable of maintaining that shape. The tube is to carry oxygen and has a first end and a second end. The first end is releasably connectable to an oxygen delivery source. To the second end of the tube is secured an end of a rigid elbow. An oxygen delivery passageway extends from that end of the elbow to its other end. An oxygen diffuser is connected to that other end of the elbow. The diffuser comprises a body having a wall, the interior surface of which wall is of generally concave configuration. The wall circumscribes a centrally positioned oxygen outlet communicating with that other end of the elbow so as to receive oxygen from the elbow and direct the flow of oxygen delivered from the elbow generally towards the patient's nose and mouth. Flexible wings are secured to the tube, between its ends, the wings extending outwardly to either side. An elongated flexible strap is secured to and extends between the wings, the strap to extend around a patient's head and secure the wings in position to hold the diffuser proximal to the patient's nose and mouth.

In a preferred embodiment of the present invention, the elbow is further provided with a carbon dioxide monitor passageway extending from one end of the elbow to the other. This passageway is independent from, and does not communicate with, the oxygen delivery passageway. A carbon dioxide intake, formed of a concave-shape wall, is centrally secured within the diffuser body wall. The carbon dioxide intake fills a significant part of the interior of that body. The carbon dioxide intake wall circumscribes a carbon dioxide intake port which communicates with the carbon dioxide monitor passageway at said one end of the elbow and the other end of the elbow is adapted to receive a carbon dioxide monitor tube, also communicating with the carbon dioxide monitor passageway, during use to collect and deliver carbon dioxide collected by the carbon dioxide intake from the vicinity of the patient's nose and mouth to a carbon dioxide monitor.

The device according to the present invention provides a lightweight, effective patient oxygen delivery device which is economical and effective. It is ideal for use in emergency rooms and ambulance environments, and may be used during medical procedures where a simple and economical, but effective way to deliver oxygen to a patient is required.

BRIEF DESCRIPTION OF THE DRAWINGS

These and other objects and advantages of the invention will become apparent upon reading the following detailed description and upon referring to the drawings in which.

Figure 1:
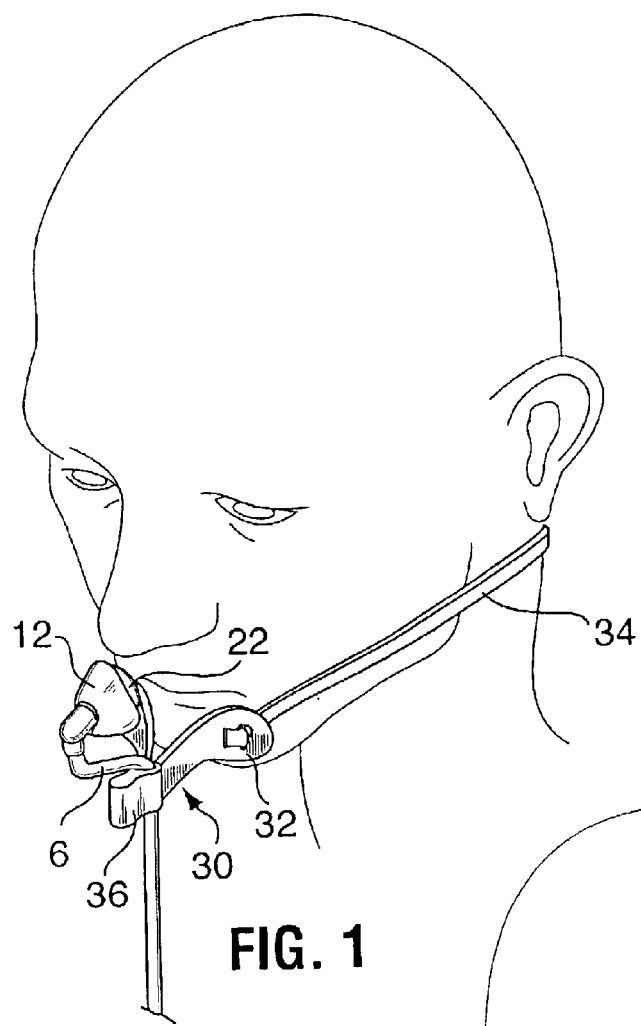
FIG. 1 is a perspective view of a oxygen delivery device according to the present invention illustrated as being supported on a patient's chin.

While the invention will be described in conjunction with an illustrated embodiment, it will be understood that it is not intended to limit the invention to such embodiment. On the contrary, it is intended to cover all alternatives, modifications and equivalents as may be included within the spirit and scope of the invention as defined by the appended claims.

DETAILED DESCRIPTION OF THE PREFERRED EMBODIMENTS

In the following description, similar features in the drawings have been given similar reference numerals.

Figure 3:
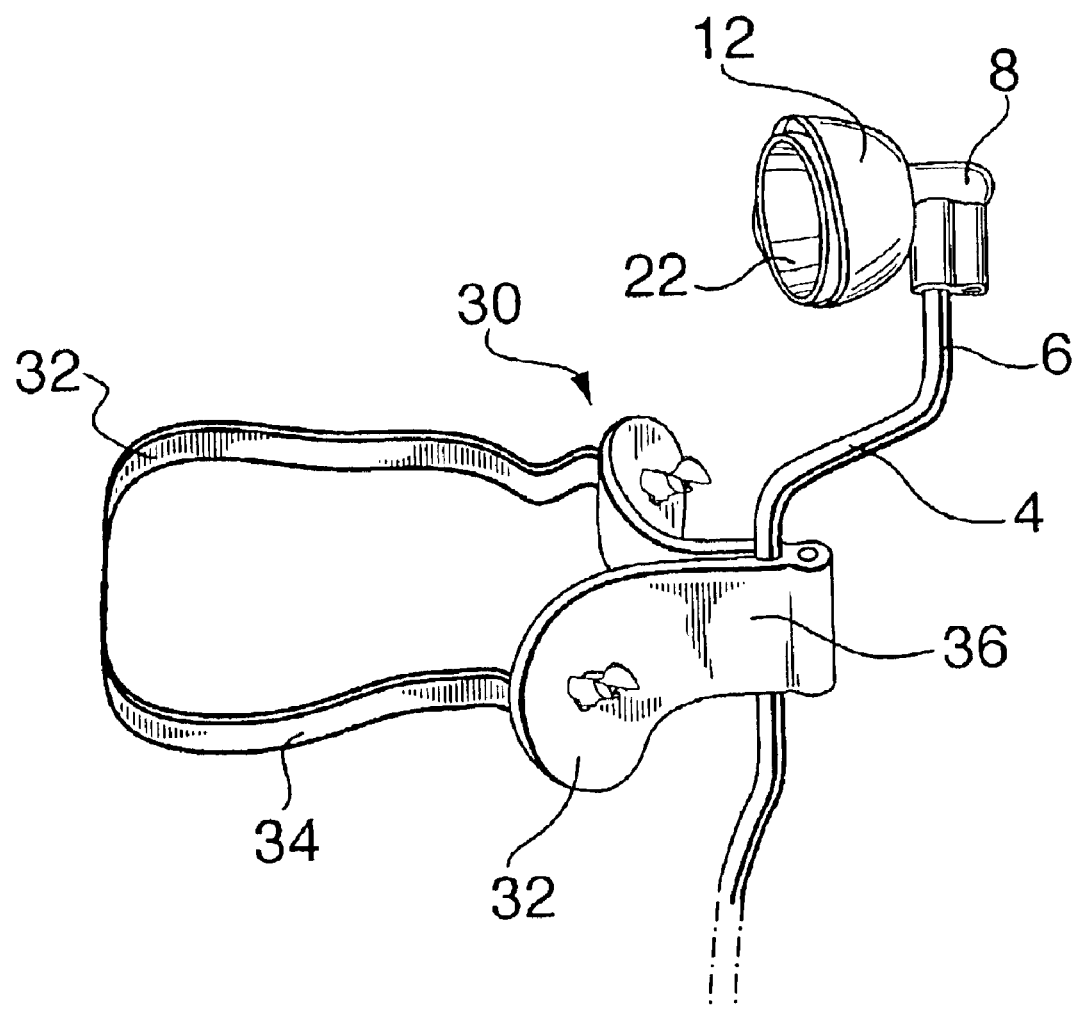
FIG. 3 is an enlarged, perspective view of the devise of FIG. 1.
Figure 5:
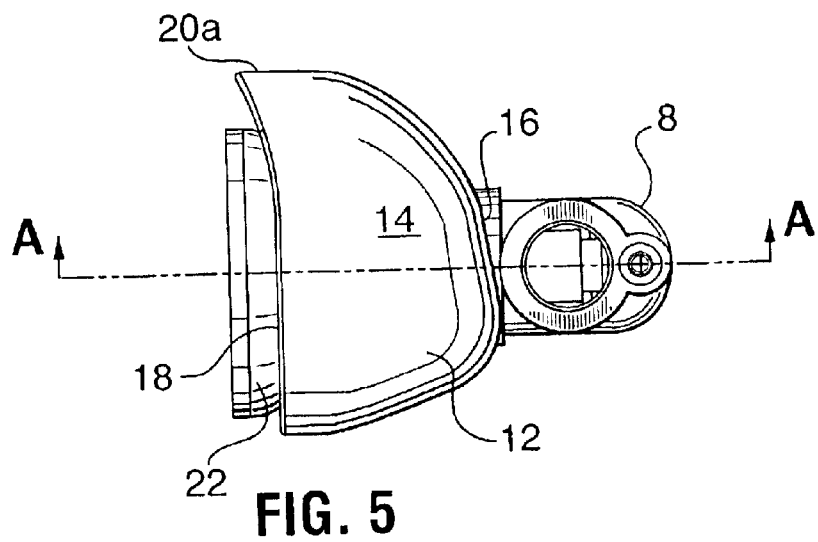
FIG. 5 is a side elevation partial view of the device of FIG. 1.
Figure 6:
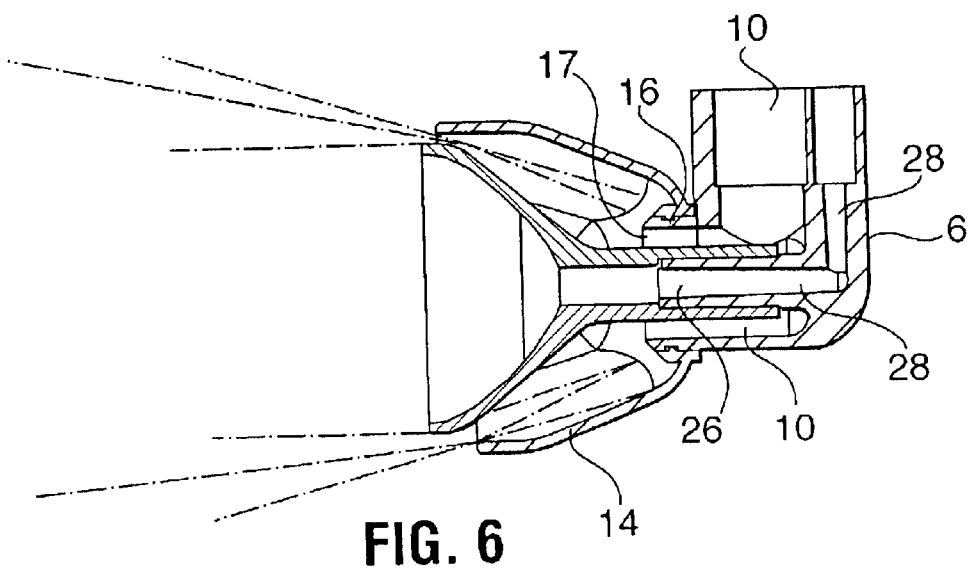
FIG. 6 is a section view of the device, along line A—A of FIG. 5.

Turning to FIG. 1, there is shown a lightweight oxygen delivery device (2), in operation and worn by a patient. The device comprises an elongated oxygen delivery tube (4) which is bendable to a particular shape and which can maintain that shape. In the illustrated embodiment, this feature is achieved by a wire (6) embedded in tube (4) during its manufacture. At one end of oxygen delivery tube (4) is a rigid elbow (8), provided with an oxygen delivery passageway (10) extending from one end of the elbow to the other (FIG. 5), oxygen delivery tube (4) communicating with that passageway. An oxygen diffuser (12) is connected to the other end of elbow (8) as illustrated. This diffuser has a body formed from a wall (14), of cup-shaped appearance, extending from a base (16) which circumscribes an oxygen outlet (17) which communicates with the oxygen delivery passageway (10) of elbow (8). Wall (14) extends from that base, upwardly and outwardly to an edge (18) of triangular peripheral contour (FIG. 3). The peripheral corners (20) are rounded, with one of the corners (20a), intended to be the uppermost corner when in use, and the proximal portions of the wall edge (18), being raised with respect to the other corners and their proximal wall edge portions as illustrated, to facilitate the direction of oxygen towards a patient's nose and mouth. This construction, with protruding corner (20a) and proximal edges of the wall (14), being positioned proximal to the patient's nose when in use, and the wider triangular portion at the bottom proximal to a patient's mouth, provides optimal oxygen delivery to a patient.

Figure 2:
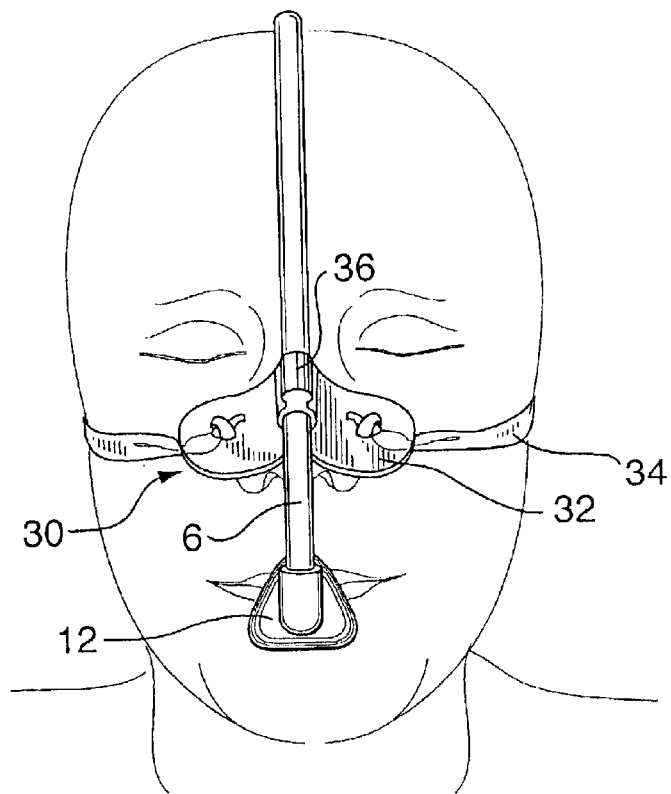
FIG. 2 is perspective view of the oxygen delivery device according to FIG. 1, as supported on a patient's nose.

Within the cup-shaped wall (14) of diffuser (12) is centrally positioned a carbon dioxide intake (22) formed of a concave, preferably hemispheric-shaped wall (24). The carbon dioxide intake (22), as can be seen in FIGS. 2 and 3, fills a significant part of the interior of the diffuser (12). To permit greater flexibility of device (2), diffuser (12) and carbon dioxide intake (22) are secured to one end of elbow (8) so as to rotate 360° on it. In this way, the proper orientation of diffuser (12) with respect to the patient's nose and mouth can be achieved.

Figure 4:
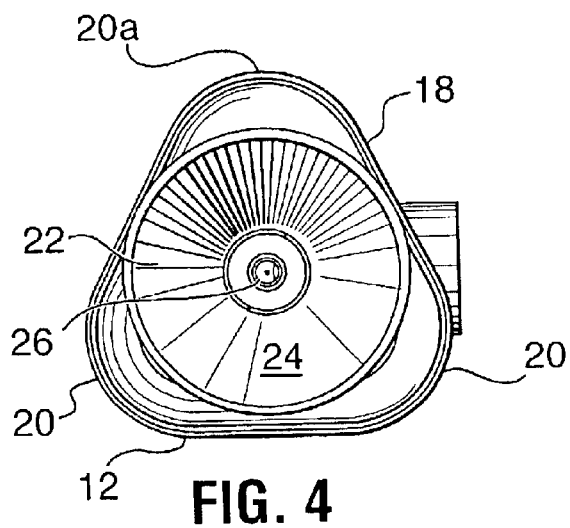
FIG. 4 is an elevation partial view from the front of the device of FIG. 1.

Wall (24) of carbon dioxide intake (22) circumscribes a carbon dioxide intake port (26) which communicates with a carbon dioxide monitor passageway (28) formed in elbow (8). Carbon dioxide monitor passageway (28) is separate from and does not communicate with oxygen delivery passageway (10) in elbow (8). At the other end of passageway (28) a carbon dioxide monitor tube (29) (phantom, FIG. 1) may be secured, that tube to communicate with a carbon dioxide monitor (not shown) when the device is in use. In this matter, carbon dioxide exhaled by the patient can be collected by carbon dioxide intake (22), from the vicinity of the patient's nose and mouth, and passed to the carbon dioxide monitor, while at the same time oxygen is being delivered from an oxygen source (again not shown), through oxygen delivery tube (4) and oxygen diffuser (12) to the patient's nose and mouth area. As can be seen in FIG. 4, it is preferable that the carbon dioxide intake wall (24) extends outwardly beyond the edges of the wall (14) of diffuser (12). It has been found in tests that this particular construction of diffuser and carbon dioxide intake provides both an effective plume of oxygen for delivery to the nose and mouth area of a patient, while at the same time enabling an effective carbon dioxide monitoring of the patient's exhaled breath, when the diffuser is positioned as illustrated.

To ensure that the diffuser 12 and carbon dioxide intake (24) are properly positioned with respect to a patient's nose and mouth during use of the device, a flexible arrangement 30 is secured to oxygen delivery tube 4 as illustrated, the arrangement having wings 32 extending outwardly to either side as illustrated. An elongated flexible strap 34 is secured to and extends between the wings, the strap 34 extending around the patient's head, when the device is in use, thereby securing the wings in position (for example on a patient's chin, as illustrated in FIG. 1, or on a patient's nose, as illustrated in FIG. 2) thereby to hold the diffuser proximal to the patient's nose and mouth. Integrally formed with wings 32, to their rear, is an attachment sleeve 36 which provides an aperture or a pair of apertures, as required, through which oxygen delivery tube 4 and carbon dioxide monitor tube 29 will pass, and by which the arrangement (30) is secured to tube (4).

The device (2) according to the present invention is easy and economical to manufacture and easy and effective to use. It avoids many of the problems of conventional oxygen masks and cannula arrangements and is lightweight and comfortable for the patient.

Thus, it is apparent that there has been provided in accordance with the invention a lightweight oxygen delivery device for a patient that fully satisfies the objects, aims and advantages set forth above. While the invention has been described in conjunction with illustrated embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

What is claimed is:

1. A lightweight oxygen delivery device for a patient comprising:
   an oxygen diffuser connected to an oxygen supply tube, the diffuser comprising a body having a wall, an interior surface of which wall is of generally concave configuration with a triangular peripheral contour and rounded corners, to direct a flow of oxygen generally towards the patient's nose and mouth;
   a carbon dioxide intake formed of a concave-shape wall centrally secured within the diffuser body wall, the carbon dioxide intake filling a significant part of the interior of that body, such that the carbon dioxide intake blocks most of the oxygen diffuser but leaves the rounded corners of the triangular peripheral contours unobstructed to deliver oxygen out of the top rounded corner directing oxygen toward the nose of the user and leaves the bottom rounded corners of the triangular peripheral contours unobstructed to direct oxygen toward the mouth of the user;
   flexible wings secured to the tube, the wings extending outwardly to either side, and an elongated flexible strap secured to and extending between the wings, the strap, when the device is in operation, to extend around a patient's head and secure the wings in position to hold the diffuser proximal to the patient's nose and mouth.

2. A device according to claim 1, wherein the oxygen supply tube is an elongated tube, the tube being bendable to a particular shape and capable of maintaining that shape, the tube to carry oxygen and having, a first end and a second end, the first end to be releasably connectable to an oxygen delivery source, and
   a rigid elbow having a pair of ends and an oxygen delivery passageway extends between those ends, one of those ends being secured to the second end of the tube 4.

3. A device according to claim 2, wherein the elbow is further provided with a carbon dioxide monitor passageway extending from one end of the elbow to the other, this passageway independent from and not communicating with the oxygen delivery passageway, and wherein a carbon dioxide intake formed of a concave-shape wall is centrally secured within the diffuser body wall, the carbon dioxide intake filling a significant part of the interior of that body, the carbon dioxide intake wall circumscribing a carbon dioxide intake port which communicates with the carbon dioxide monitor passageway at said one end of the elbow, the other end of the elbow being adapted to receive a carbon dioxide monitor tube in communicating with the carbon dioxide monitor passageway during use to collect and deliver to a carbon dioxide monitor, carbon dioxide collected by the carbon dioxide intake from the vicinity of the patient's nose and mouth.

4. A device according to claim 3, wherein the carbon dioxide intake wall extends outwardly beyond the wall of the diffuser body.

5. A device according to claim 1, wherein the diffuser wall is of cup-shaped appearance, extending from a base where the oxygen outlet is positioned, outwardly and upwardly to an edge of triangular peripheral contour.

6. A device according to claim 5, wherein the corners of the edge are rounded and one of the corners, intended when in use to be the uppermost corner, and portions of the wall edge proximal to said one of the corners, are slightly raised with respect to the other corners and edge portions, to facilitate direction of oxygen towards a patients nose and mouth.

7. A device according to claim 6, wherein the diffuser and carbon dioxide intake are provided with a swivel attachment to the elbow whereby the diffuser and carbon dioxide intake may be rotated 360 on the elbow.

8. A device according to claim 1, wherein a wire is embedded in the oxygen supply tube to permit bending of the tube to a particular shape and maintaining of that shape.

9. A device according to claim 3, wherein the carbon dioxide intake is formed of a hemispheric-shaped wall.

* * * * *